July 25, 1950 K. L. RUSTERHOLZ Plant Pat. 969

AVOCADO TREE

Filed March 24, 1949

INVENTOR.
KATHERINE LILLIAN RUSTERHOLZ
BY B. J. Crowd
ATTORNEY

Patented July 25, 1950 Plant Pat. 969

UNITED STATES PATENT OFFICE

969

AVOCADO TREE

Katherine Lillian Rusterholz, Whittier, Calif.

Application March 24, 1949, Serial No. 83,262

1 Claim. (Cl. 47—62)

My discovery relates to a new and distinct avocado tree which is an improvement over previously known varieties and which stands frost very well and produces excellent fruit.

The original tree is a seedling of unknown parentage. Lyon seeds were available to the planter and as the tree and fruit have some characteristics of the Lyon, it is possible that the tree grew from a Lyon seed. The parent seed was planted during the year 1924 on the south side of the house which is located at 326 South Bright Avenue, Whittier, California.

The tree bears a good, medium size, winter maturing fruit which is available when good avocado fruits are scarce. The tree has good growth habits and the general appearance of the fruit is excellent. The fruit has almost no neck and it is practically free from fibre. The fruit keeps in excellent manner and there is no internal rotting prior to full ripening of the fruit.

The characteristics of the tree and fruit vary slightly under various conditions of climate, moisture, topography, soil and care, but the desirable characteristics are present under all growing conditions.

This new variety has been successfully asexually reproduced by budding, with the employment of thin skinned Mexican seedlings as root stock at 326 Bright Avenue, Whittier, California.

In the accompanying drawing.

*The tree*

Growth habits: The tree is tall, more upright than spreading, and is quite uniform in general appearance. The tree became so high it had to be topped and at the present time is about thirty feet high and has a circumference of approximately 45 inches. The tree has a good subterranean root system. The tree is characterized by rapid growth of the budded stock.

Bearing habits: The fruit crop is medium heavy and in some years there is a tendency towards overbearing. There is no premature dropping of fruit.

Hardiness: The tree stands cold weather very well. During the unusually cold winter of 1948–49 the parent tree did not show frostbite although a Fuerte tree growing alongside the parent tree and exposed in a similar manner was badly frostbitten.

Maturity: My original tree fruited at 7 years from the time of planting the seed. Budded trees come into bearing at an early age.

Blossoming: The present avocado starts to blossom in February. The blossoms appear in small bunches which are evenly distributed.

Fruit placement: The fruit is well distributed about the tree. The fruit hangs pendant on long, light green stems which vary in length usually from 6 to 8 inches and with many pairs of fruits on a single stem.

Ripening date: The fruit matures from about November 15 to January 15.

Foliage:

*Quantity.*—Abundant, with very light drop during blooming season.

*Color.*—The mature leaves are waved or rippled along the edges and are light green in color, being somewhat lighter in shade than the Fuerte. The lower surface is of a lighter shade of green than the upper surface.

*Size.*—From 8 to 10 inches long and with a width of about 4 inches.

*Shape.*—Normal.

*Texture and veining.*—The principal leaf veins are quite pronounced while minor veins are less distinct, and the leaf as a whole is smooth and not puckered. The upper surface of the leaves is smooth but not glossy. The leaves have from 7 to 10 ribs, with the mid rib of many of the leaves relatively straight where the growth of the leaf has not been obstructed.

*Distribution.*—The leaves are well distributed over the tree and afford fruit protection.

*The fruit*

Weight: The weight of the fruit is from 8 ounces to a pound, the average weight being about 11 ounces when mature.

Figure 1:
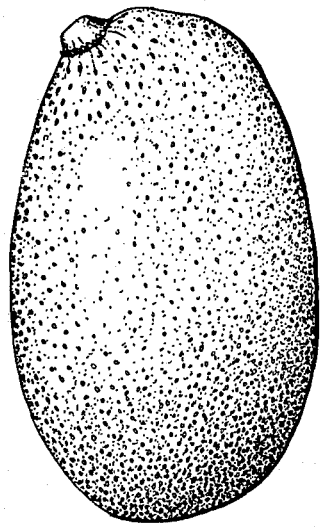
Fig. 1 is a side elevation of an avocado fruit, showing the button and embodying the characteristics of my invention.
Figure 2:
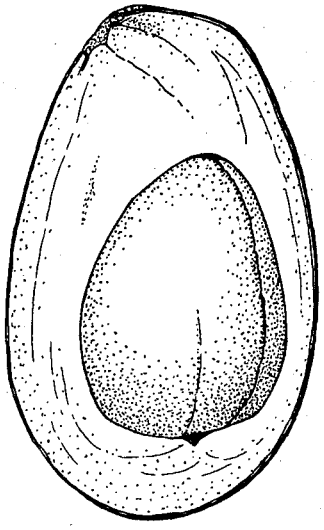
Fig. 2 is a central, sectional view through a fruit with the button removed.
Figure 3:
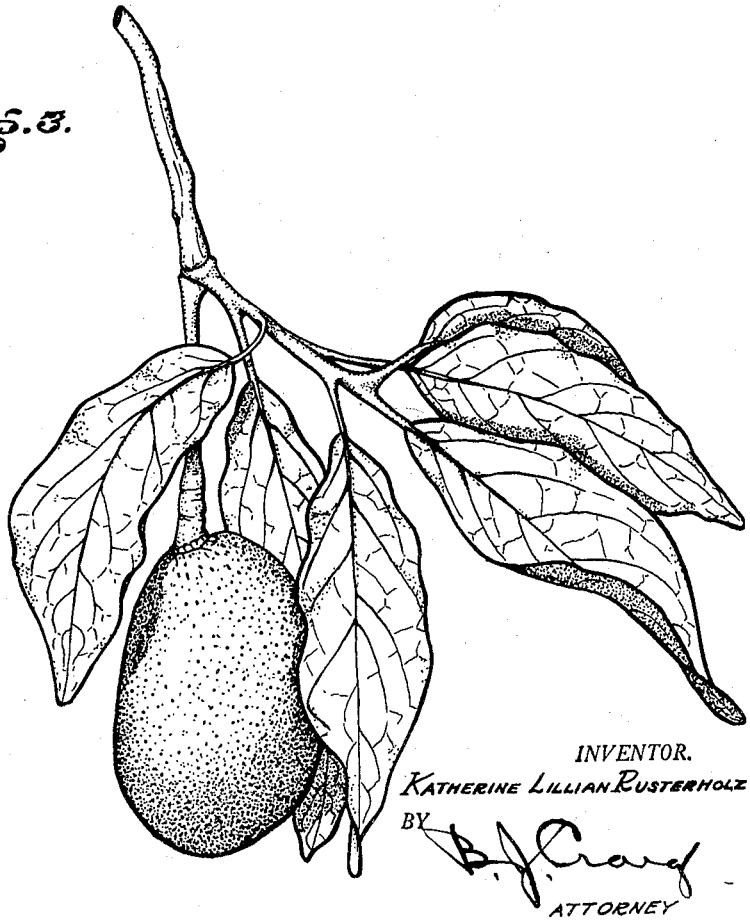
Fig. 3 is an elevation showing a branch with leaves, stem and a fruit.

Shape: The fruit is of oval shape, slightly tending to pyriform. A characteristic of some of the fruit on each tree is that at the stem end at one side of the button there is an area which is almost plane in contour. This plane or blunt portion is characteristic and the pitch of the plane of this blunt portion is often almost perpendicular to the longitudinal axis of the fruit, as shown in Figs. 1 and 2 of the drawing, or the blunt portion may be inclined at an angle to the longitudinal axis of the fruit as shown in Fig. 3.

Skin: The color of the fruit is common to that of the Guatemalan, being dark, glossy green when mature on the tree. The skin of the picked fruit gradually turns to a mixed purple and green and then dark purple. The surface spots are a light brown and are small in size and medium in number.

Aspect: Smooth and glossy.

Texture: The skin of the fruit is thin for a Guatemalan and is strong, rather tough but pliant, so that the fruit is well protected and the shipping qualities are excellent. The skin is without blemish or defects. The skin does not scab or crack.

Button: The button is large and the line of division between the button and stem is not particularly noticeable nor is the button cavity, which is usually disposed slightly at one side of the longitudinal axis of the fruit, large. The button is firmly attached to the stem and the stem attachment to the tree is strong so that high winds do not displace the fruit.

Flesh:

*Color.*—The flesh is a light green color.

*Flavor.*—The flavor is mild, similar to the Fuerte.

*Texture.*—The flesh is of butter-like consistency, with practically no fibre content.

*Oil content.*—Very high, as rich as the Fuerte.

Seed:

*Shape.*—Generally oval, with no pronounced sharp apex at either end. The seed cavity is well placed to afford a pleasing appearance.

*Size.*—The average seed weighs about 1½ ounces and the seed is small for the size of the fruit.

*Texture.*—The surface of the seed is smooth and the seed is hard.

*Seed coat.*—The seed coat is smooth, brown and relatively thick and adheres tightly to the seed.

*Separability.*—The arrangement of the seed in the fruit and the relative size of the two is such that when the seed is removed the seed coat nearly always is withdrawn with the seed, but occasionally some of the seed coat remains in the cavity. The seed is tight in the seed cavity.

Having thus described my invention, I claim: The new and distinct variety of avocado tree substantially as herein shown and described distinguished as to novelty by its winter ripening, medium-large sized fruits of purple color when fully matured, having a skin which is thin for a Guatemalan type and pliant, with the fruit borne on medium length stems, with a medium sized, tight seed and with creamy colored flesh which is smooth with practically no fibre and which has a butter-like consistency.

KATHERINE LILLIAN RUSTERHOLZ.

No references cited.